(12) United States Patent
Bickhart et al.

(10) Patent No.: US 10,441,771 B2
(45) Date of Patent: Oct. 15, 2019

(54) HEMOSTASIS VALVES AND RELATED COMPONENTS AND METHODS

(71) Applicants: Merit Medical Systems, Inc., South Jordan, UT (US); Abiomed, Inc., Danvers, MA (US)

(72) Inventors: Bryan Bickhart, Ardmore, PA (US); Christopher A. Heine, Schwenksville, PA (US); Mary L. Milone, Telford, PA (US); John Murphy, Danvers, MA (US)

(73) Assignees: Merit Medical Systems, Inc., South Jordan, UT (US); Abiomed, Inc., Danvers, MA (US)

( * ) Notice: Subject to any disclaimer, the term of this patent is extended or adjusted under 35 U.S.C. 154(b) by 115 days.

(21) Appl. No.: 15/267,675

(22) Filed: Sep. 16, 2016

(65) Prior Publication Data

US 2017/0080200 A1    Mar. 23, 2017

Related U.S. Application Data

(60) Provisional application No. 62/220,684, filed on Sep. 18, 2015.

(51) Int. Cl.
*A61M 39/06* (2006.01)
*A61M 39/00* (2006.01)

(52) U.S. Cl.
CPC . *A61M 39/0606* (2013.01); *A61M 2039/0072* (2013.01); *A61M 2039/062* (2013.01); *A61M 2039/064* (2013.01); *A61M 2039/066* (2013.01); *A61M 2207/00* (2013.01)

(58) Field of Classification Search
CPC .... A61M 2039/0072; A61M 2039/062; A61M 2039/064; A61M 2039/066; A61M 2207/00; A61M 39/0606
See application file for complete search history.

(56) References Cited

U.S. PATENT DOCUMENTS

| | | | |
|---|---|---|---|
| 5,104,389 A * | 4/1992 | Deem | A61M 39/0606 604/167.02 |
| 5,935,112 A | 10/1999 | Stevens et al. | |
| 6,142,981 A | 11/2000 | Heck et al. | |
| 7,582,070 B2 | 9/2009 | Goode et al. | |
| 8,523,822 B2 | 9/2013 | Nardeo et al. | |
| 2012/0221024 A1 | 8/2012 | Sutton et al. | |
| 2012/0245527 A1 | 9/2012 | Stephens et al. | |
| 2014/0343512 A1 | 11/2014 | Fischer et al. | |
| 2015/0157843 A1 | 6/2015 | Pepin et al. | |

OTHER PUBLICATIONS

International Search Report and Written Opinion dated Dec. 8, 2016 for PCT/US2016/052114.
European Search Report dated Apr. 26, 2019 for EP16847374.2.

* cited by examiner

*Primary Examiner* — Imani N Hayman
(74) *Attorney, Agent, or Firm* — Stoel Rives LLP

(57) ABSTRACT

Hemostasis valves and hemostasis valve assemblies can be coupled to a proximal end of an introducer sheath to prevent blood loss through the proximal end of the introducer sheath. Some hemostasis valve assemblies may include an elastomeric member with a variable-width channel that is designed to form a liquid-tight seal over elongate members of different diameter or a single elongate member of variable diameter.

19 Claims, 12 Drawing Sheets

HEMOSTASIS VALVES AND RELATED COMPONENTS AND METHODS

RELATED APPLICATIONS

This application claims priority to U.S. Provisional Application No. 62/220,684, filed on Sep. 18, 2015 and titled, "Hemostasis Valves and Related Components and Methods," which is hereby incorporated by reference in its entirety.

TECHNICAL FIELD

The present disclosure relates generally to the field of medical devices and related methods. More particularly, some embodiments relate to hemostasis valves and hemostasis valve assemblies for preventing or minimizing fluid loss during medical procedures, such as interventional and/or diagnostic procedures.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1A:
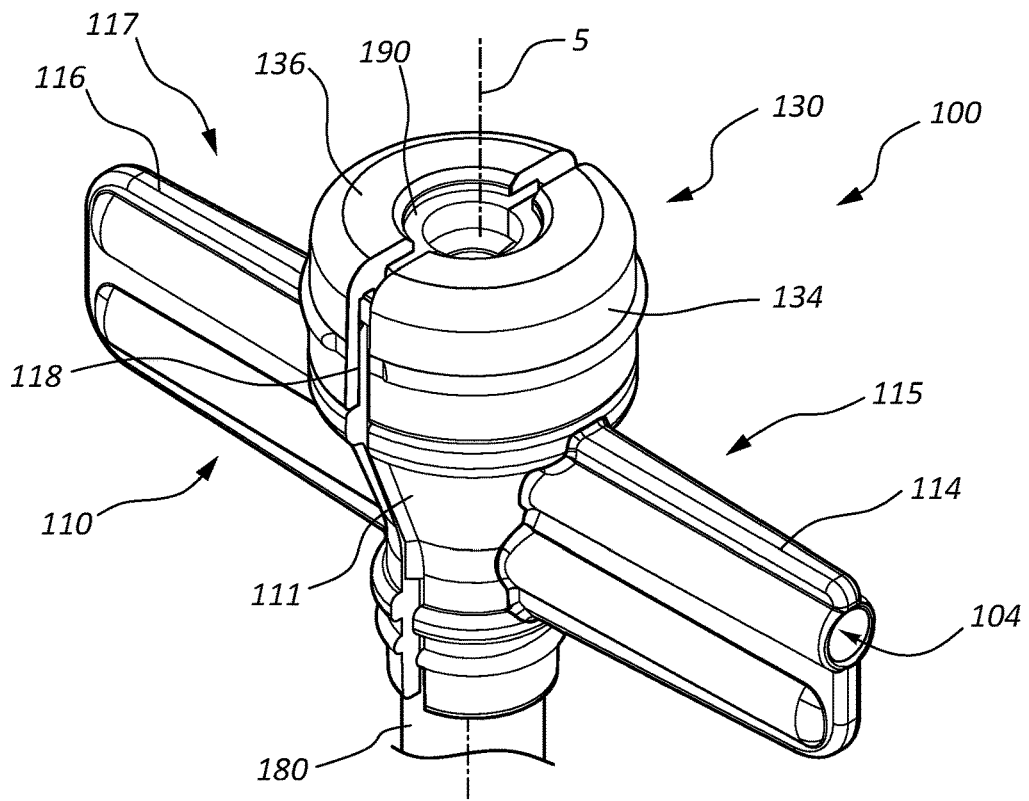
FIG. 1A is a perspective view of a hemostasis valve assembly.

In many medical procedures (e.g., angiography, angioplasty, stent placement, etc.), an introducer sheath may be inserted into the vasculature of a patient to provide an access point for inserting other medical instruments into the patient. To prevent or minimize blood loss through the introducer sheath, a hemostasis valve assembly may be attached to the proximal end of the introducer sheath. With the hemostasis valve assembly and the introducer sheath in place, elongate medical instruments, such as guidewires, catheters, and other medical implements, may then be inserted through the hemostasis valve assembly and advanced through the introducer sheath.

In some instances, the elongate medical instruments that are advanced through the hemostasis valve assembly may have different sizes (e.g., different outer diameters). In other or further instances, the size of the outer diameter of a single elongate medical instrument that is passed through the hemostasis valve assembly may vary along the length of the elongate medical instrument. Some hemostasis valves and hemostasis valve assemblies disclosed herein are sized to allow passage of a portion of an elongate instrument that includes an outer diameter of greater than or equal to 9 Fr, 12 Fr, and/or 14 Fr without damaging the valve. In other or further embodiments, hemostasis valves disclosed herein may form a liquid-tight seal around various sized diameters. For example, in some embodiments, a hemostasis valve is configured to form a liquid-tight seal around a relatively small-diameter elongate medical instrument, a medium-diameter elongate medical instrument, and a relatively large-diameter elongate medical instrument. For instance, in some embodiments, a hemostasis valve is configured to form a liquid-tight seal around an elongate instrument with a diameter of 1-2 Fr, an elongate instrument with a diameter of 4-7 Fr, and an elongate instrument with a diameter of 8-10 Fr.

In some embodiments, the hemostasis valve and/or introducer sheath are configured to be removed from an elongate member that extends through the hemostasis valve and/or introducer sheath without retracting the hemostasis valve and/or introducer sheath over a proximal end of the elongate member. For example, in some embodiments, the hemostasis valve and/or introducer sheath may be split by a practitioner. The split hemostasis valve and/or introducer sheath may then be removed from the elongate member without retracting such components over a proximal end of the elongate member.

Some of the hemostasis valves described herein can be used in a variety of different procedures. For example, in an exemplary medical procedure, an introducer sheath is introduced into the vasculature of a patient in any suitable fashion (e.g., via insertion into the femoral artery of a patient). A hemostasis valve may be coupled to a proximal end of the introducer sheath to prevent blood loss through the proximal end of the introducer sheath. Once the introducer sheath and hemostasis valve are in place, an elongate medical instrument may be inserted through the hemostasis valve, passed through the introducer sheath, and advanced within the vasculature of the patient. The elongate medical instrument may be left within the vasculature for as long as needed. In some circumstances, a practitioner may desire to remove the introducer sheath and the hemostasis valve assembly from around the elongate instrument without retracting such components over a proximal end of the device. For example, while the elongate medical instrument is in use, the practitioner may snap, rip, tear, split, cut, or otherwise separate portions of the hemostasis valve assembly and/or introducer sheath from one another, thereby allowing a practitioner to remove such components from around the elongate medical instrument.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluid interaction. Two components may be coupled to each other even though they are not in direct contact with each other. The phrase "attached to" refers to interaction between two or more entities that are in direct contact with each other and/or are separated from each other only by a fastener of any suitable variety. The phrase "fluid communication" is broad enough to refer to arrangements in which a fluid (e.g., a gas or a liquid) can flow from one element to another element when the elements are in fluid communication with each other. Unless otherwise stated, all ranges include both endpoints and all numbers between the endpoints.

The terms "proximal" and "distal" are opposite directional terms. The distal end of a device or component is the end of the device or component that is furthest from the practitioner during ordinary use. The proximal end refers to the opposite end, or the end nearest the practitioner during ordinary use. A hemostasis valve or hemostasis valve assembly is in a "resting state" when no elongate member (e.g., an elongate medical device) is disposed across of the hemostasis valve. The term "longitudinal axis," when used with reference to a hemostasis valve assembly, refers to an imaginary line extending proximally to distally through the center of the hemostasis valve assembly.

Figure 1B:
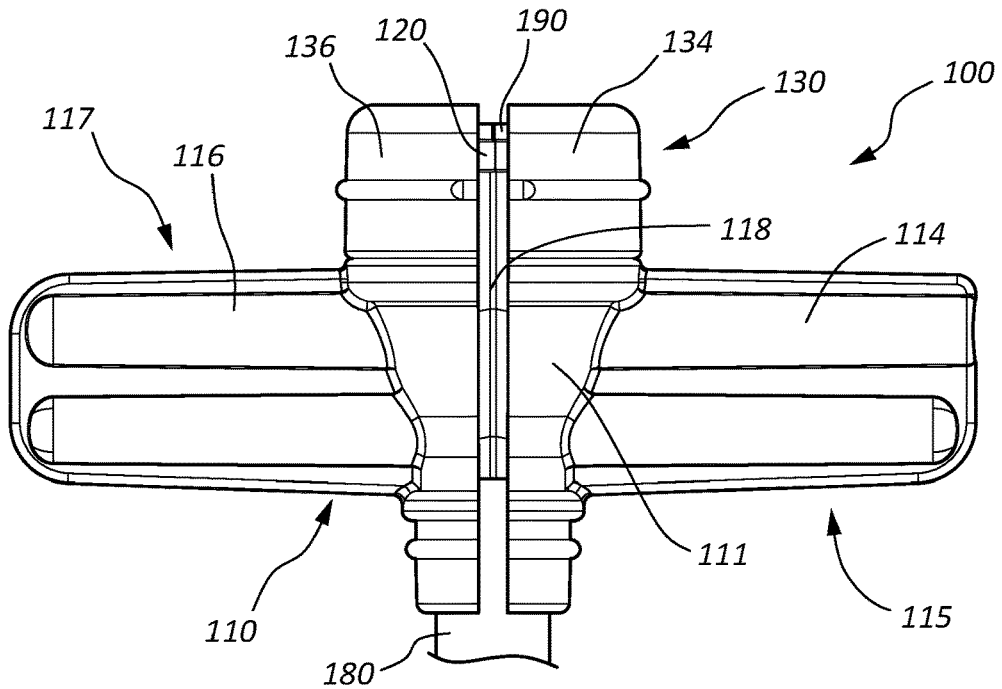
FIG. 1B is a front view of the hemostasis valve assembly of FIG. 1A.
Figure 1C:
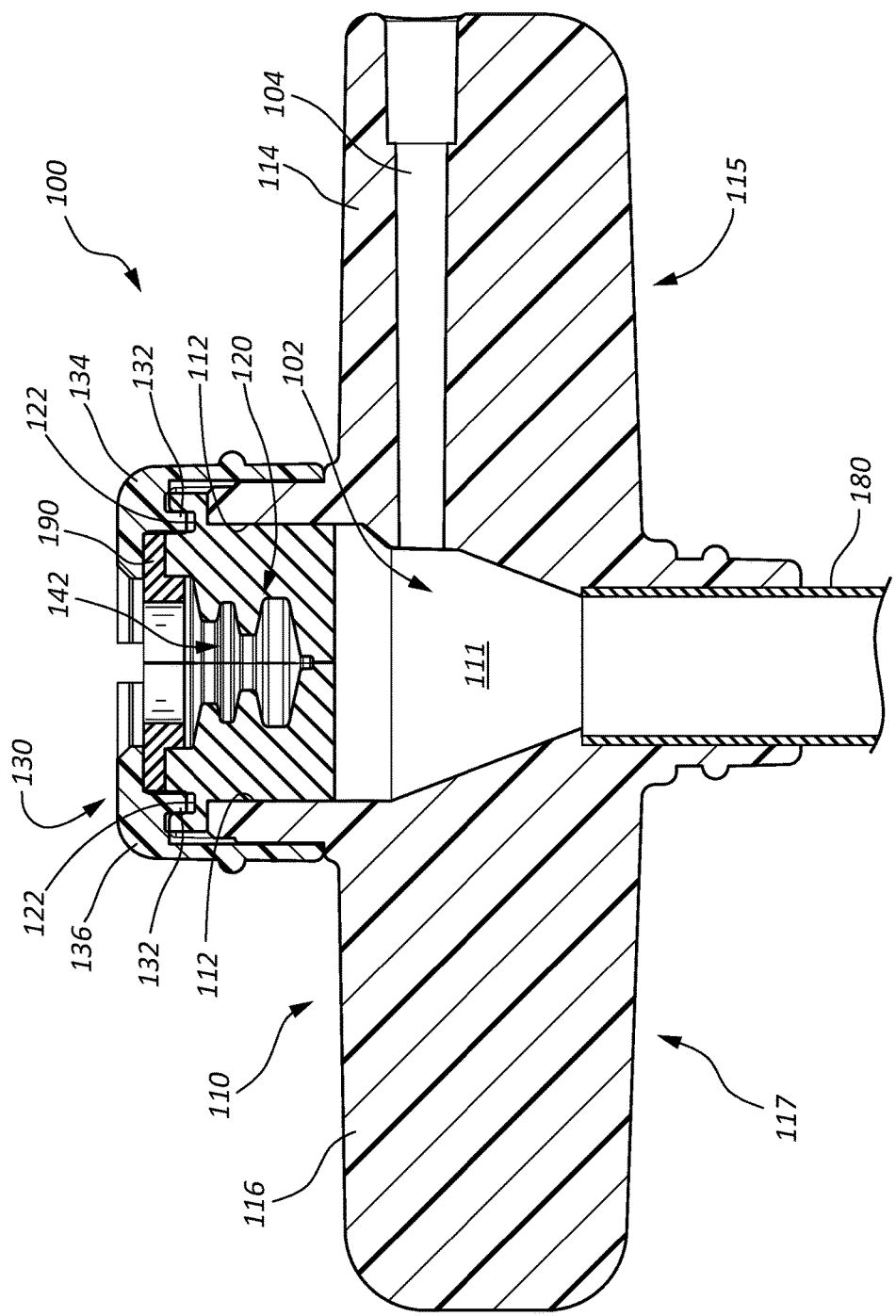
FIG. 1C is a cross-sectional front view of the hemostasis valve assembly of FIG. 1A.
Figure 1D:
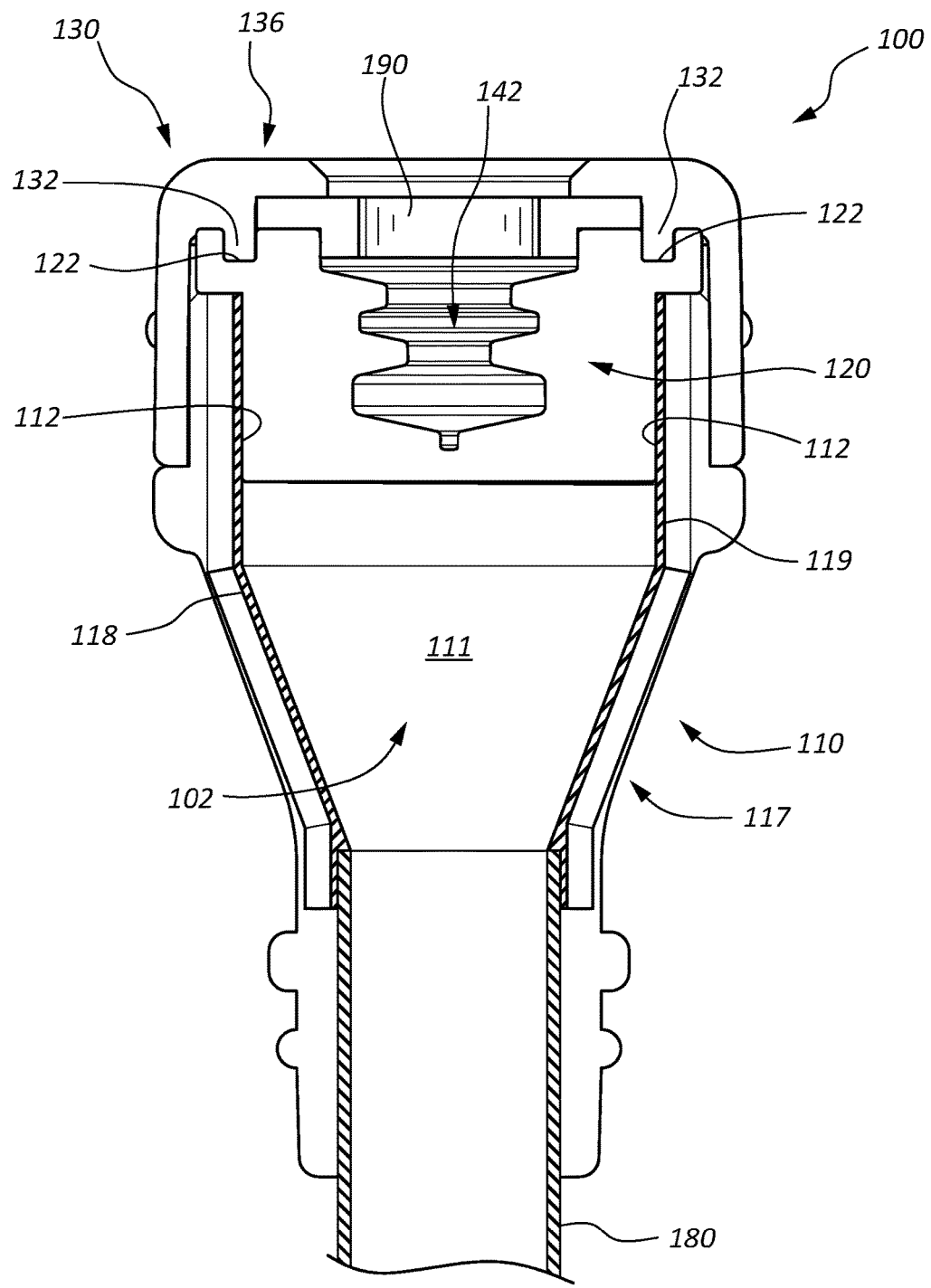
FIG. 1D is a cross-sectional side view of the hemostasis valve assembly of FIG. 1A.

FIGS. 1A-1D provide alternative views of a hemostasis valve assembly 100. More particularly, FIG. 1A provides a perspective view of the hemostasis valve assembly 100. FIG. 1B provides a front view of the hemostasis valve assembly 100. FIG. 1C provides a cross-sectional front view of the hemostasis valve assembly 100. And FIG. 1D provides a cross-sectional side view of the hemostasis valve assembly 100. With reference to FIGS. 1A-1D, the hemostasis valve assembly 100 may include a housing 110 (which may alternatively be referred to as a hub), a valve (e.g., an elastomeric member 120), and a cap 130.

The housing 110 may include a central region 111. The central region 111 may define a first lumen 102 that extends along the longitudinal axis 5 of the hemostasis valve assembly 100. The first lumen 102 may be configured to accommodate one or more elongate members (e.g., elongate medical instruments) that may be used in a medical procedure. In some embodiments, the central region 111 may include a first reduced-thickness portion 118 and a second reduced-thickness portion 119. For example, a first reduced-thickness portion 118 may extend proximally to distally along the front of the housing 110, while a second reduced-thickness portion 119 may extend proximally to distally along the back of the housing 110. The reduced-thickness portions 118, 119 may be configured to facilitating breakage or splitting of the housing 110 along the reduced-thickness portions 118, 119. For example, the housing 110 may be configured to break into two separate portions 115, 117 that are separated by the reduced-thickness portions 118, 119.

The housing 110 may also include a plurality of arms 114, 116 that extend radially outward from the central region 111. Stated differently, a first arm 114 and a second arm 116 may extend radially outward relative to a longitudinal axis 5 of the hemostasis valve assembly 100. The arms 114, 116 may be configured to facilitate splitting of the hemostasis valve assembly 100 (or components thereof). Stated differently, the first arm 114 and the second arm 116 may be configured to separate portions 115, 117 of the housing 110 from one another to permit removal of the housing 110 from an elongate member that extends through the elastomeric member 120 without retracting the housing 110 over the proximal end of the elongate member. For example, a practitioner may apply a first force to a central region 111 of the housing 110 and opposing forces on the arms 114, 116, thereby causing the housing 110 to break and/or snap. In some embodiments, the housing 110 may break and/or snap along the first reduced-thickness portion 118 and the second reduced-thickness portion 119, thereby breaking the housing 110 into two separate pieces 115, 117. Additional disclosure relating to breakage of the housing 110 is described below in connection with FIG. 6C.

In some embodiments, the housing 110 may also define a second lumen 104 that is in fluid communication with and extends laterally from the first lumen 102. The second lumen 104 may be configured to couple to a secondary device. For example, fluid from a secondary device may be delivered into the hemostasis valve assembly 100 via the second lumen 104.

The housing 110 may be coupled to a proximal portion of an introducer sheath 180 in any suitable manner. For example, in some embodiments, the housing 110 is molded to, integrally formed with, or fused to, the introducer sheath 180. In other embodiments, the housing 110 is coupled to the introducer sheath 180 via an adhesive, frictional engagement, or via some other mechanism.

In some embodiments, the housing 110 also defines and/or forms a cylindrical inner diameter 112. In the depicted embodiment, the cylindrical inner diameter 112 is sized to accommodate an elastomeric member 120. In some embodiments, the portion of the housing 110 that defines the cylindrical inner diameter 112 is disposed proximal of the remaining portions of the housing 110.

The elastomeric member 120 of the hemostasis valve assembly 100 may be configured to be at least partially disposed within the cylindrical inner diameter 112 defined by the housing 110. The elastomeric member 120 may form a variable-width channel 142 that extends partway through the elastomeric member 120. The channel 142 may be centered around and extend along the longitudinal axis 5 of the hemostasis valve assembly 100. As described in further detail below in connection with other figures, the elastomeric member 120 may be configured to form a liquid-tight seal around an elongate member (not shown) that extends through the hemostasis valve assembly 100.

In some embodiments, the elastomeric member 120 includes a recess 122 disposed adjacent a proximal end of the elastomeric member 120. For example, in the depicted embodiment, the recess 122 extends in circular fashion around a longitudinal axis 5 of the hemostasis valve assembly 100.

The cap 130 of the hemostasis valve assembly 100 may be secured to the housing 110 by adhesive, detents, and/or some other coupling mechanism, thereby securing the elastomeric member 120 at least partially within the inner diameter 112 formed by the housing 110. More particularly, in some embodiments, the cap 130 includes one or more protrusions 132 that extend distally from a proximal portion of the cap 130. When the cap 130 is secured to the housing 110, the one or more protrusions 132 of the cap 130 may engage with the recess 122 of the elastomeric member 120. The interaction between the one or more protrusions 132 and the recess 122 may secure (or more fully secure) the elastomeric member 120 at least partially within the inner diameter 112 of the housing 110. In some embodiments, the cap 130 is formed from two unconnected portions. For example, in the depicted embodiment, the cap 130 is formed from a first portion 134 and a second portion 136 that are separately coupled to the housing 110. In such embodiments, the portions 134, 136 of the cap 130 may separate from one another as the housing 110 is split.

In some embodiments, the hemostasis valve assembly 100 may also include one or more pieces of foam 190 that are disposed between the cap 130 and the elastomeric member 120. The one or more pieces of foam 190 may hold lubricious fluid that eases insertion and removal of various elongate members (e.g., therapy devices). The one or more pieces of foam 190 may also provide additional structural support adjacent the proximal end of the elastomeric member 120. In the depicted embodiment, the foam 190 is donut-shaped.

Hemostasis valves assemblies, such as hemostasis valve assembly 100, may be manufactured in any suitable manner. For example, in some embodiments, manufacturing the hemostasis valve assembly 100 involves obtaining a housing 110 and an elastomeric member 120. The elastomeric member 120 may be formed from any suitable material. For example, in some embodiments, the elastomeric member 120 is formed from silicone rubber. The elastomeric member 120 may be placed or otherwise disposed within (or at least partially disposed within) an inner diameter 112 defined by the housing 110.

The inner diameter 112 defined by the housing 110 may radially compress the elastomeric member 120. Stated differently, when disposed within the inner diameter 112 defined by the housing 110, the elastomeric member 120 may be compressed toward a longitudinal axis 5 of the hemostasis valve assembly 100. In some embodiments, the width (i.e., outer diameter) of the elastomeric member 120 when at least partially disposed within the cylindrical inner diameter 112 is between 97% and 94% of the width of the elastomeric member 120 when uncompressed. In other embodiments, the width of the compressed elastomeric member 120 is less than 94% of the width of the elastomeric member 120 when uncompressed.

Once the elastomeric member 120 is at least partially disposed within the cylindrical inner diameter 112 of the housing 110, the cap 130 may be coupled to the housing 110, thereby securing the elastomeric member 120 within the cylindrical inner diameter 112 of the housing 110. The cap 130 may be secured to the housing 110 in any suitable fashion. For example, in some embodiments the cap 130 is secured to the housing 110 via an adhesive. In other or further embodiments, the cap 130 is secured to the housing 110 via one or more detents and/or other coupling elements. In some embodiments, one or more protrusions 132 of the cap 130 may engage with a recess 122 of the elastomeric member 120 as the cap 130 is coupled to the housing 110.

Figure 2A:
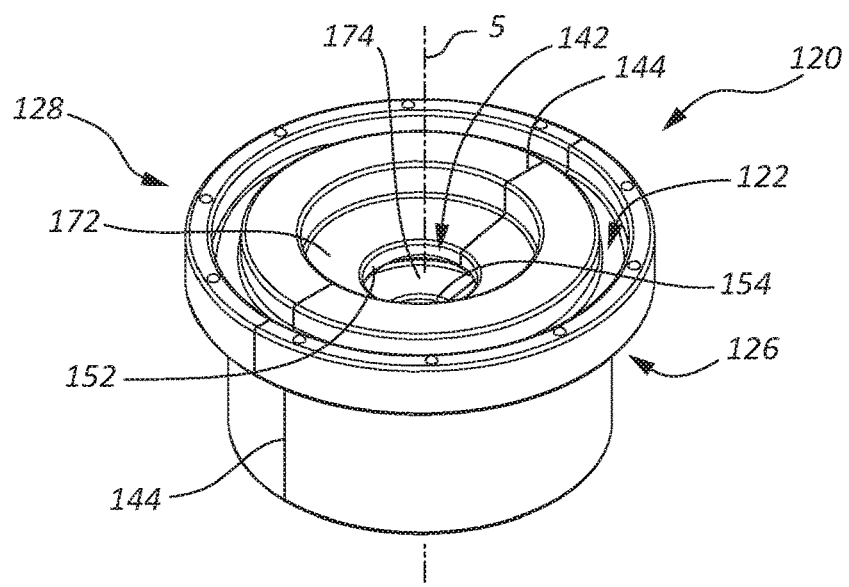
FIG. 2A is a perspective view of an elastomeric member of the hemostasis valve assembly of FIG. 1A.
Figure 2B:
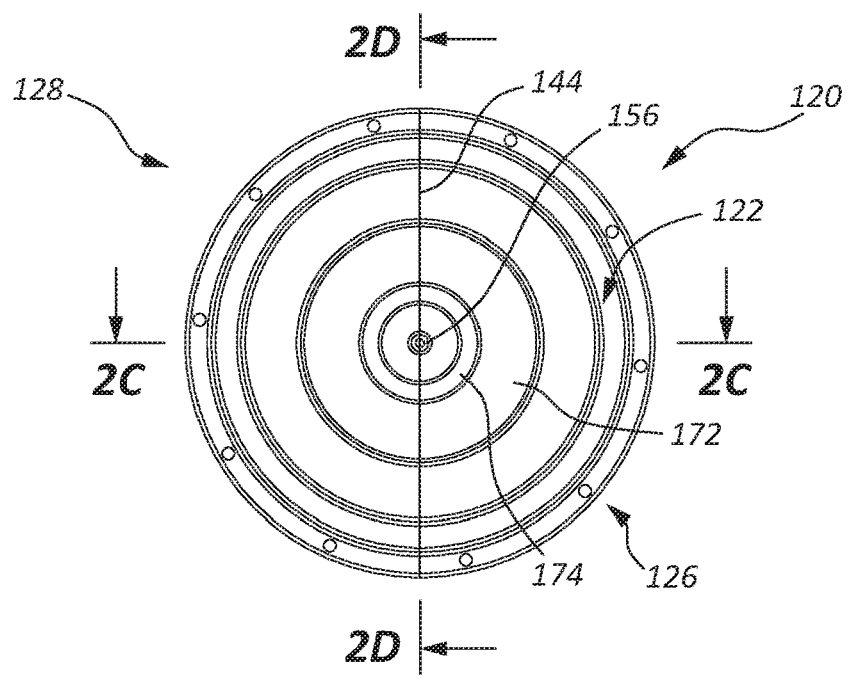
FIG. 2B is a top view of the elastomeric member of FIG. 2A.
Figure 2C:
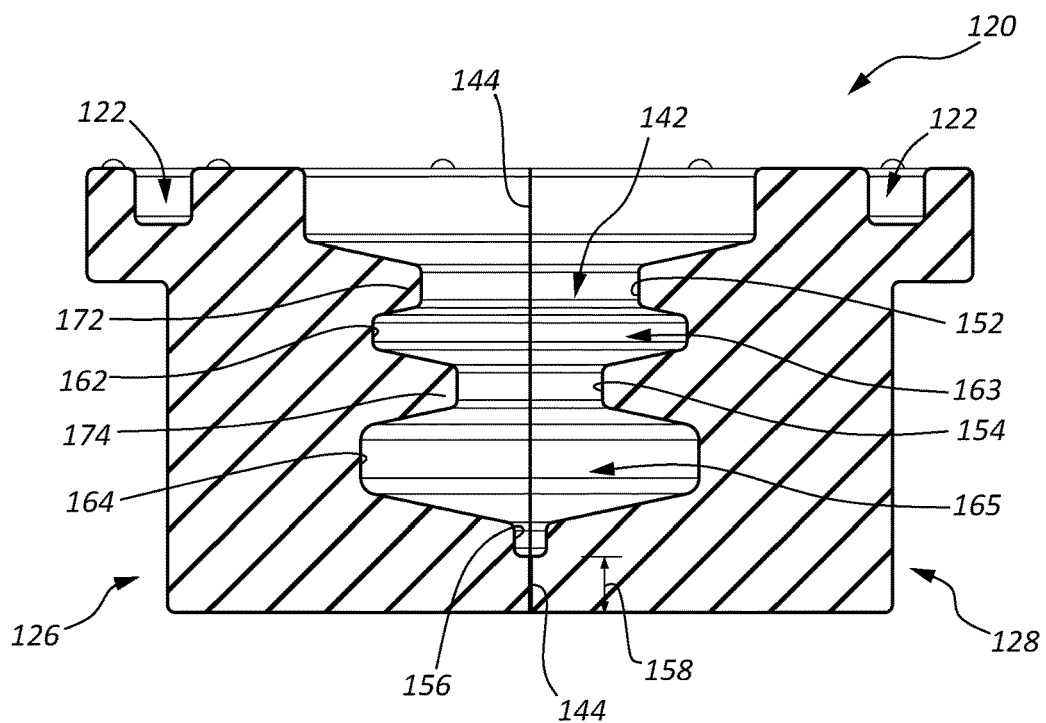
FIG. 2C is a cross-sectional front view of the elastomeric member of FIG. 2A.
Figure 2D:
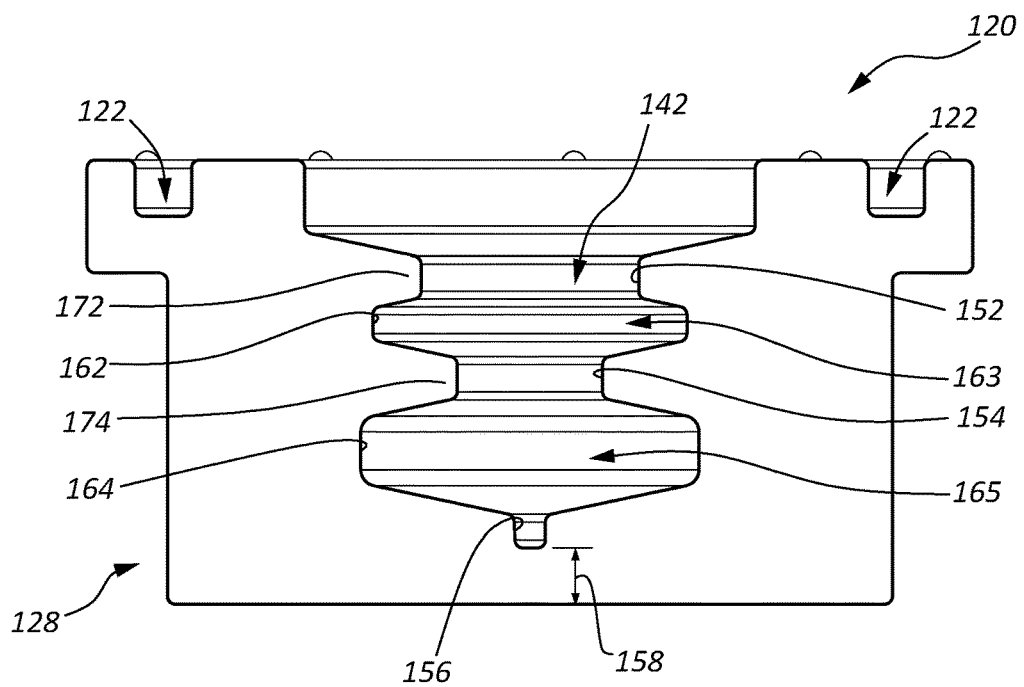
FIG. 2D is a cross-sectional side view of the elastomeric member of FIG. 2A.

FIGS. 2A and 2B provide alternative views of the elastomeric member 120 of the hemostasis valve assembly 100 shown in FIGS. 1A-1C. More particularly, FIG. 2A provides a perspective view of the elastomeric member 120. FIG. 2B provides a top view of the elastomeric member 120 (showing the proximal end of the elastomeric member 120). FIG. 2C provides a cross-sectional front view of the elastomeric member 120 through line 2C-2C of FIG. 2B. And FIG. 2D provides a cross-sectional side view of the elastomeric member 120 through line 2D-2D of FIG. 2B.

With reference to FIGS. 2A-2D, the elastomeric member 120 may include one or more recesses 122 for engagement with one or more protrusions of the cap to secure the elastomeric member 120 to the housing. For example, in some embodiments, a single circular recess 122 extends into a proximal surface of the elastomeric member 120. In other or further embodiments, the elastomeric member 120 includes one or more recesses in some other configuration for mating with one or more protrusions of a cap.

The elastomeric member 120 may form a channel 142 that extends partway through the elastomeric member 120 when the hemostasis valve assembly 100 is in the resting state (i.e., no elongate member is disposed across the elastomeric member 120).

The elastomeric member 120 may include a plurality of inward-extending protrusions 172, 174. For example, in the depicted embodiment, the elastomeric member 120 includes a first protrusion 172 and a second protrusion 174 that is disposed distal of the first protrusion 172. The elastomeric member 120 may also include a plurality of inner surfaces. More particularly, in the depicted embodiment, the elastomeric member 120 includes a first sealing surface 152 (e.g., an innermost surface of the first protrusion 172), a second sealing surface 154 (e.g., an innermost surface of the second protrusion 174), and a third sealing surface 156. In some embodiments, the first sealing surface 152 forms a first cylindrical surface having a diameter of between approximately 3 mm and 8 mm. Stated differently, when the hemostasis valve assembly 100 is in the resting state, the first cylindrical surface may have a diameter that corresponds to the outer diameter of an elongate member that is between 9 Fr and 24 Fr, such as between 9 Fr and 12 Fr, 9 Fr and 14 Fr, or 12 Fr and 24 Fr. In some embodiments, the second sealing surface 154 forms a second cylindrical surface having a resting diameter of between approximately 2 mm and 2.67 mm. Stated differently, the sealing surface 154 may have a resting diameter that corresponds to the outer diameter of an elongate member that is between 6 Fr and 8 Fr. In some embodiments, the sealing surface 156 forms a third cylindrical surface having a diameter of between 0.35 mm to approximately 0.97 mm. Other diameters are also contemplated and within the scope of this disclosure.

In some embodiments, the first sealing surface 152 forms a first cylindrical surface having a first height of between 0.25 mm and 1.5 mm. For example, in some embodiments, the first cylindrical surface has a height of between 0.25 mm and 1.3 mm, between 0.25 mm and 1.0 mm, between 0.25 mm and 0.75 mm, between 0.25 mm and 0.45 mm; between 0.30 mm and 1.5 mm, between 0.50 mm and 1.5 mm, between 0.75 and 1.5 mm, or between 1.0 mm and 1.5 mm. In some embodiments, the height of the first sealing surface is 0.35±0.10 mm; 0.45±0.10 mm; 0.55±0.10 mm; 0.65±0.10 mm; 0.75±0.10 mm; 0.85±0.10 mm; 0.9±0.10 mm; 1.00±0.10 mm; 1.10±0.10 mm; 1.20±0.10 mm; 1.30±0.10 mm; 1.40±0.10 mm.

In some embodiments, the height of the second sealing surface 154 forms a second cylindrical surface having a second height of between 0.25 mm and 1.5 mm. For example, in some embodiments, the second cylindrical surface has a height of between 0.25 mm and 1.3 mm, between 0.25 mm and 1.0 mm, between 0.25 mm and 0.75 mm, between 0.25 mm and 0.45 mm; between 0.30 mm and 1.5 mm, between 0.50 mm and 1.5 mm, between 0.75 mm and 1.5 mm, or between 1.0 mm and 1.5 mm. In some embodiments, the height of the first sealing surface is 0.35±0.10 mm; 0.45±0.10 mm; 0.55±0.10 mm; 0.65±0.10 mm; 0.75±0.10 mm; 0.85±0.10 mm; 0.9±0.10 mm; 1.00±0.10 mm; 1.10±0.10 mm; 1.20±0.10 mm; 1.30±0.10 mm; 1.40±0.10 mm.

The elastomeric member 120 also includes a first relief surface 162 and a second relief surface 164. The first relief surface 162 may form a first relief space 163, and the second relief surface 164 may form a second relief space 165. The channel 142 may, at least in part, be defined by a plurality of inner surfaces (e.g., sealing surfaces and relief surfaces) of the elastomeric member 120.

In some embodiments, the first relief surface 162 includes a cylindrical surface having a height of between 0.30 mm and 2.5 mm. For example, in some embodiments, the cylindrical surface of the first relief surface 162 has a height of between 0.30 mm and 0.50 mm; between 0.30 mm and 0.75 mm; between 0.30 mm and 1.0 mm; between 0.30 mm and 1.3 mm; between 0.30 mm and 1.5 mm; between 0.30 mm and 2.0 mm; between 0.30 mm and 2.5 mm, between 2.0 mm and 2.5 mm; between 1.5 mm and 2.5 mm, between 1.3 mm and 2.5 mm, between 1.0 mm and 2.5 mm; between 0.75 mm and 2.5 mm; or between 0.50 mm and 2.5 mm. In some embodiments, the height of the cylindrical surface of the first relief surface 162 is 0.50±0.20 mm, 0.75±0.20 mm; 1.0±0.3 mm; 1.5±0.3 mm; 2.0±0.3; or 2.5±0.3 mm.

In some embodiments, the second relief surface 164 includes a cylindrical surface having a height of between 0.30 mm and 2.5 mm. For example, in some embodiments, the cylindrical surface of the second relief surface 164 has a height of between 0.30 mm and 0.50 mm; between 0.30 mm and 0.75 mm; between 0.30 mm and 1.0 mm; between 0.30 mm and 1.3 mm; between 0.30 mm and 1.5 mm; between 0.30 mm and 2.0 mm; or between 0.30 mm and 2.5 mm; between 2.0 mm and 2.5 mm; between 1.5 mm and 2.5 mm, between 1.3 mm and 2.5 mm, between 1.0 mm and 2.5 mm; between 0.75 mm and 2.5 mm; or between 0.50 mm and 2.5 mm. In some embodiments, the height of the cylindrical surface of the second relief surface 164 is 0.50±0.20 mm, 0.75±0.20 mm; 1.0±0.3 mm; 1.5±0.3 mm; 2.0±0.3; or 2.5±0.3 mm.

In some embodiments, such as the depicted embodiment, the height of the cylindrical surface of the second relief surface 164 is greater than the height of the cylindrical surface of the first relief surface 162. In other embodiments, the height of the cylindrical surface of the first relief surface 162 is greater than or equal to the height of the cylindrical surface of the second relief surface 164.

As shown in FIGS. 2C and 2D, the first sealing surface 152 may be proximal of the first relief surface 162, the first relief surface 162 may be proximal of the second sealing surface 154, the second sealing surface 154 may be proximal of the second relief surface 164, and the second relief surface 164 may be proximal of the third sealing surface 156.

Each of the sealing surfaces 152, 154, 156 and each of the relief surfaces 162, 164 may define a particular diameter. For instance, the first sealing surface 152 may define a first diameter, the first relief surface 162 may define a second diameter, the second sealing surface 154 may define a third diameter, the second relief surface 164 may define a fourth diameter, and the third sealing surface 156 may define a fifth diameter.

As shown in the depicted embodiment, the sealing surfaces 152, 154, 156 are generally closer to the longitudinal axis 5 than any adjacent relief surface 162, 164. For instance, in the depicted embodiment, the diameter of the first relief surface 162 (i.e., the second diameter) is larger than the diameter of the first sealing surface 152 (i.e., the first diameter).

In some embodiments, the diameter of the second sealing surface 154 (i.e., the third diameter) differs in size from the diameter of the first sealing surface 152 (i.e., the first diameter). For example, in some embodiments, the first diameter is larger than the third diameter. In other or further embodiments, the diameter of the third sealing surface 156 (i.e., the fifth diameter) differs from the diameter of the first sealing surface 152 (i.e., the first diameter) and the diameter of the second sealing surface 154 (i.e., the third diameter). For example, in some embodiments, the fifth diameter is smaller than both the first diameter and the third diameter.

As shown in FIGS. 2A-2D, a slit 144 may extend at least partway through the elastomeric member 120. For example, in some embodiments, the slit 144 extends at least from a distal end of the elastomeric member 120 to a distal end of the channel 142. In the depicted embodiment, the slit 144 extends through an entirety of the elastomeric member 120, thereby dividing the elastomeric member 120 into separate unconnected pieces. Thus, while hatching is used in the cross-sectional view provided in FIG. 2C, no hatching is shown in FIG. 2D due to orientation of the views with respect to the slit 144. In other words, in some embodiments, the slit 144 may divide the elastomeric member 120 into a first portion 126 and a second portion 128. In such circumstances, the view provided in FIG. 2D may be identical to an analogous view of the second portion 128 of the elastomeric member when the first portion 126 and the second portion 128 of the elastomeric member 120 are separated from one another. In other embodiments, the slit 144 extends only partway through the elastomeric member 120. In some embodiments, the elastomeric member 120 is manufactured (e.g., molded) as a single piece and then cut in two pieces to form the slit 144. In other embodiments, each portion 126, 128 of the elastomeric member 120 is separately manufactured.

An elastomeric member 120 that includes two separate, unconnected pieces 126, 128 may facilitate removal of the elastomeric member 120 from around an elongate member (not shown) that extends through the elastomeric member 120. For example, when a practitioner desires to uncouple the elastomeric member 120 from around an elongate member that extends through the elastomeric member 120, the practitioner may break or split the housing into two separate portions as described elsewhere herein. By breaking the housing, the practitioner may remove the housing from around the elongate member. Without the compression forces provided by the housing, the first portion 126 and the second portion 128 of the elastomeric member 120 may then separate from one another, thereby permitting removal of the elastomeric member 120 from around the elongate member.

In other embodiments, the slit of the elastomeric member extends only partway across the elastomeric member. For example, in some embodiments, the slit extends inward from an outside edge of the elastomeric member to the longitudinal axis of the hemostasis valve assembly. In such embodiments, once the housing has been removed, the elongate member may then be removed from the elastomeric member via the slot without retracting the elastomeric member over a proximal end of the elongate member. In still other embodiments, once the housing has been removed from around the elongate member, the elastomeric member may be torn off the elongate member. Stated differently, the elastomeric member may be made from material that allows the practitioner to tear at least a portion of the elastomeric member once the housing has been removed, thereby allowing removal of the elongate member from the torn elastomeric member without retracting the elastomeric member over the proximal end of the elongate member.

As shown in FIGS. 2C and 2D, the elastomeric member 120 may include a sealing zone 158. The sealing zone 158 may form a liquid-tight seal across the slit 144 when the hemostasis valve assembly is in a resting state (i.e., when no elongate member extends through the hemostasis valve assembly). For example, when the elastomeric member 120 is under compression, an inward surface of the first portion 126 of the elastomeric member 120 may be disposed flush against an inward surface of the second portion 128 of the elastomeric member 120, thereby forming a liquid-tight seal analogous to liquid-tight seals formed by a slit-valve of a single-piece valve. Alternatively stated, when in the resting state, the channel 142 may extend from a proximal end of the elastomeric member 120 to the sealing zone 158. In some embodiments, the sealing zone 158 of the elastomeric member 120 is disposed distal of the remaining portions of the elastomeric member 120. In other embodiments, the sealing zone is disposed proximal of a distal-most end of the elastomeric member.

FIGS. 3A-5B depict the elastomeric member 120 as various elongate members 10a, 10b, and 10c of different diameter are inserted through the elastomeric member 120.

Figure 3A:
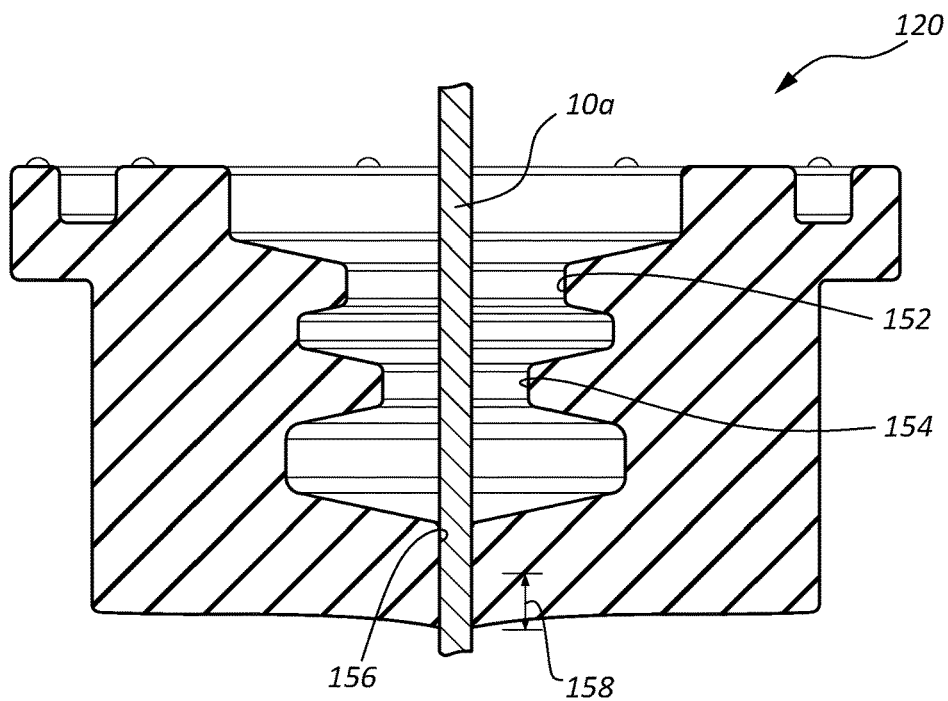
FIG. 3A is a cross-sectional front view of the elastomeric member of FIG. 2A with an elongate member of relatively small diameter extending therethrough.
Figure 3B:
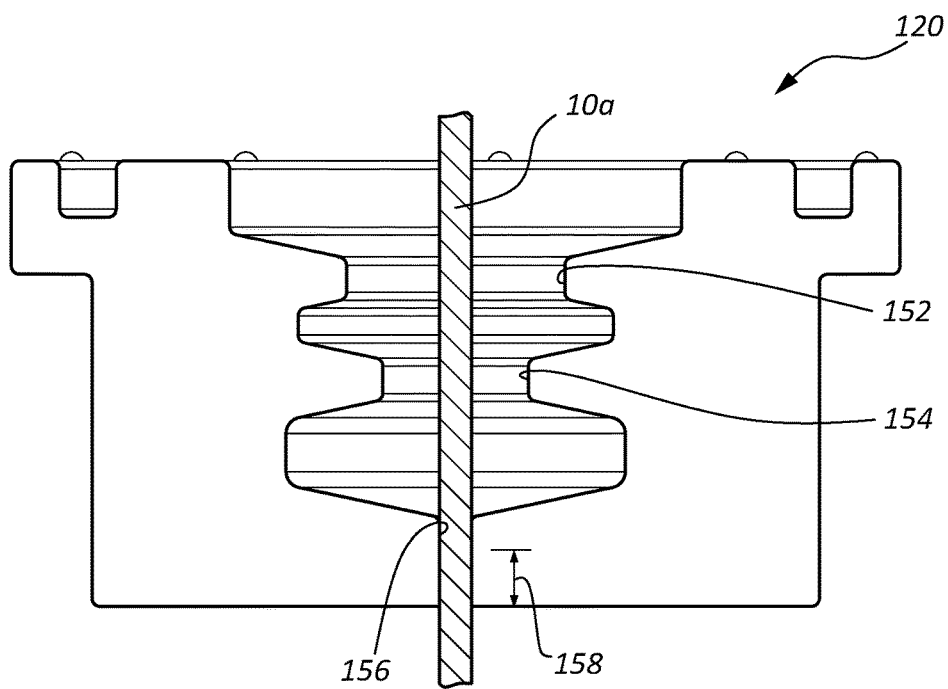
FIG. 3B is a cross-sectional side view of the elastomeric member of FIG. 3A with an elongate member of relatively small diameter extending therethrough.

For example, FIGS. 3A-3B depict alternative views of the elastomeric member 120 as an elongate member of relatively small diameter 10a (e.g., a guidewire) is inserted through the elastomeric member 120. More particularly, FIG. 3A provides a cross-sectional view of the elastomeric member 120 analogous to the view provided in FIG. 2C (i.e., perpendicular to the slit), while FIG. 3B provides a view of the elastomeric member 120 analogous to the view provided in FIG. 2D (i.e., along the slit).

As can be seen in these figures, the third sealing surface 156 may be sized to form a liquid-tight seal around the elongate member 10a (e.g., a guidewire). Stated differently, the diameter of the third sealing surface 156 (i.e., the fifth diameter) may be configured to form a liquid-tight seal around a guidewire. The first sealing surface 152 and the second sealing surface 154 do not form a liquid-tight seal around the elongate member 10a due to their larger size. Due to placement of the elongate member 10a across the elastomeric member 120, the slit may widen at and/or adjacent to the sealing zone 158 to accommodate the elongate member 10a. The portions of elastomeric member 120 that contact one another to form the sealing zone 158 may also deflect distally into open space below the elastomeric member 120 as the elongate member 10a is inserted across the elastomeric member 120.

Figure 4A:
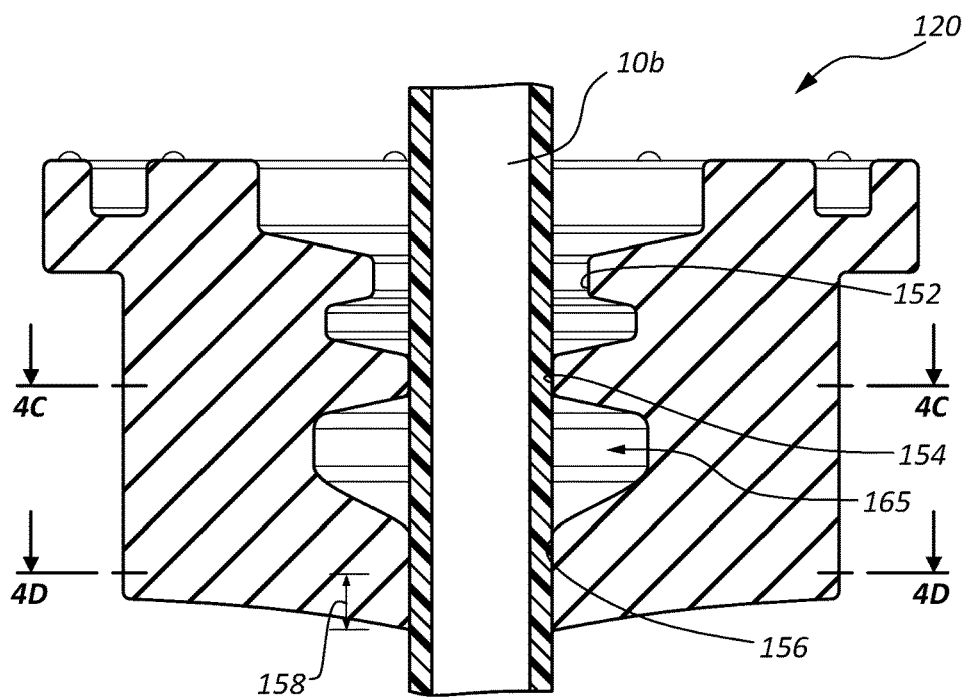
FIG. 4A is a cross-sectional front view of the elastomeric member of FIG. 2A with an elongate member of intermediate diameter extending therethrough.
Figure 4B:
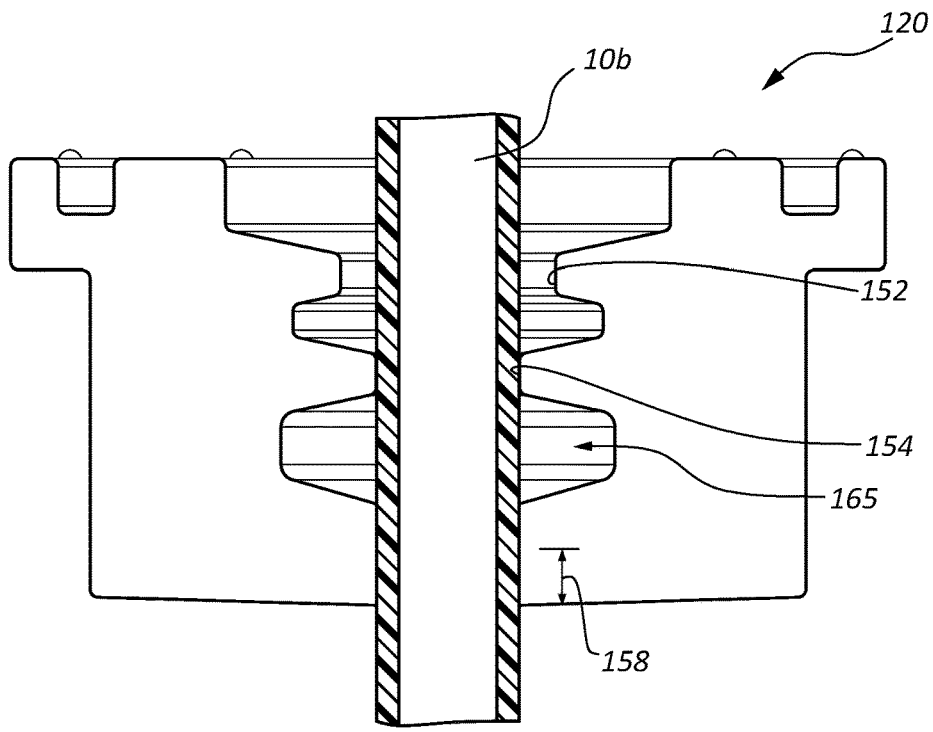
FIG. 4B is a cross-sectional side view of the elastomeric member of FIG. 4A with an elongate member of intermediate diameter extending therethrough.
Figure 4C:
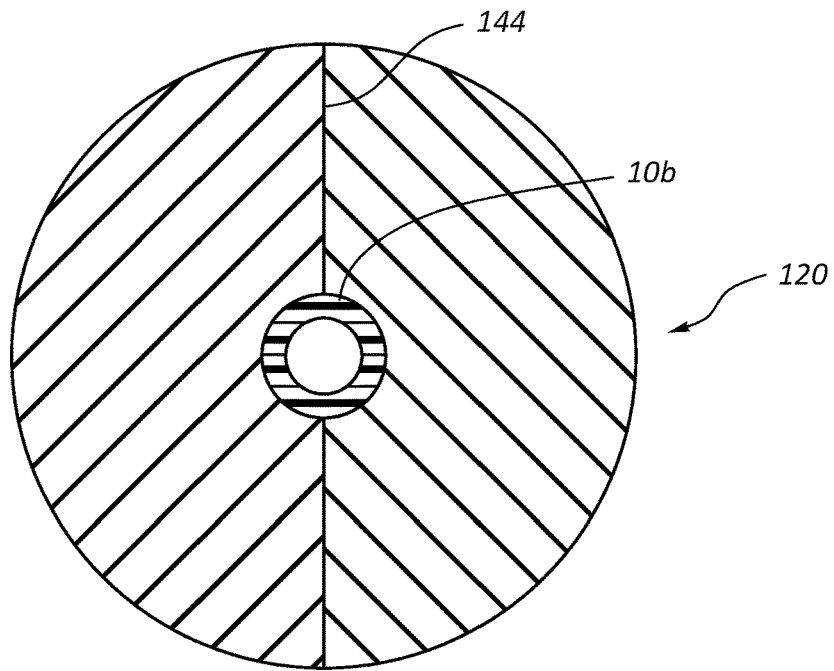
FIG. 4C is a cross-sectional view of the elastomeric member and the elongate member of FIG. 4A through line 4C-4C of FIG. 4A.
Figure 4D:
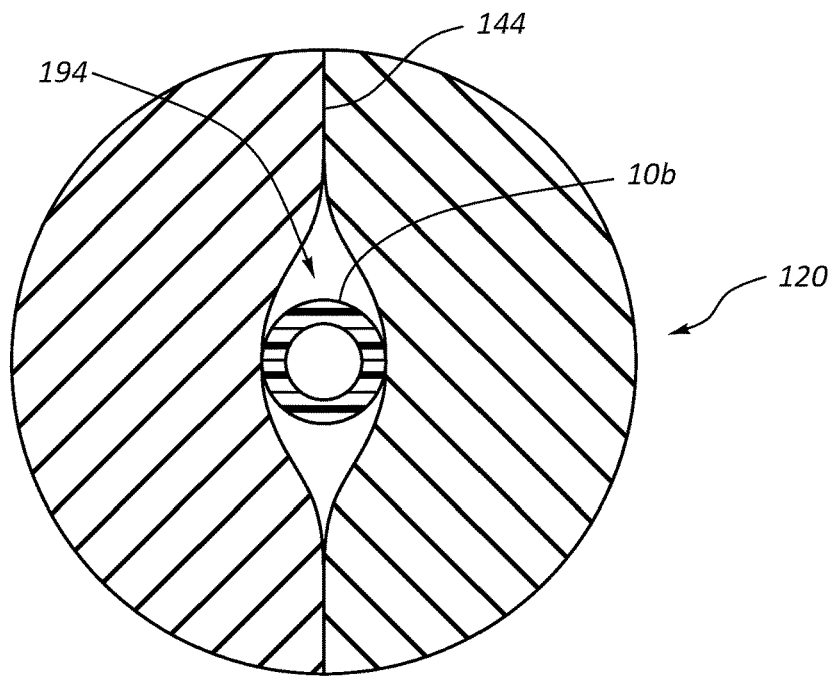
FIG. 4D is a cross-sectional view of the elastomeric member and the elongate member of FIG. 4A through line 4D-4D of FIG. 4A.

FIGS. 4A-4D provide alternative views of the elastomeric member 120 as an elongate member 10b of intermediate diameter extends across the elastomeric member 120. More particularly, FIG. 4A provides a cross-sectional front view of the elastomeric member 120 analogous to the view provided in FIG. 2C (i.e., perpendicular to the slit). FIG. 4B provides a view of the elastomeric member 120 analogous to the view provided in FIG. 2D (i.e., along the slit). FIG. 4C provides a cross-sectional view of the elastomeric member 120 through line 4C-4C of FIG. 4A. And FIG. 4D provides a cross-sectional view of the elastomeric member 120 through line 4D-4D of FIG. 4A.

As can be seen in FIGS. 4A-4D, the second sealing surface 154 is sized to form a liquid-tight seal around the elongate member 10b of intermediate diameter. The first sealing surface 152 does not form a liquid-tight seal around the elongate member 10b due to its larger size. Nor does the third sealing surface 156 form a liquid-tight seal around the elongate member 10b, as placement of the elongate member 10b across the elastomeric member 120 causes widening of the slit 144 (see FIG. 4D), thereby potentially allowing blood to flow past the third sealing surface 156. Stated differently, as the elongate member 10b is disposed across the elastomeric member 120, the slit 144 may widen to accommodate the elongate member 10b. As shown in FIG. 4D, accommodation of the elongate member 10b may result in a passageway 194 that allows blood to enter into the second relief space 165. The size and shape of the passageways 194 shown in FIG. 4D is merely exemplary. One of ordinary skill in the art, with the benefit of this disclosure, will recognize that the size and shape of passageways that permit fluid flow therethrough may differ somewhat from the passageways 194 shown in FIG. 4D. For example, in some embodiments, the size of the passageways may be smaller than shown in FIG. 4D relative to the elastomeric member 120 and/or the elongate member 10b.

Figure 5A:
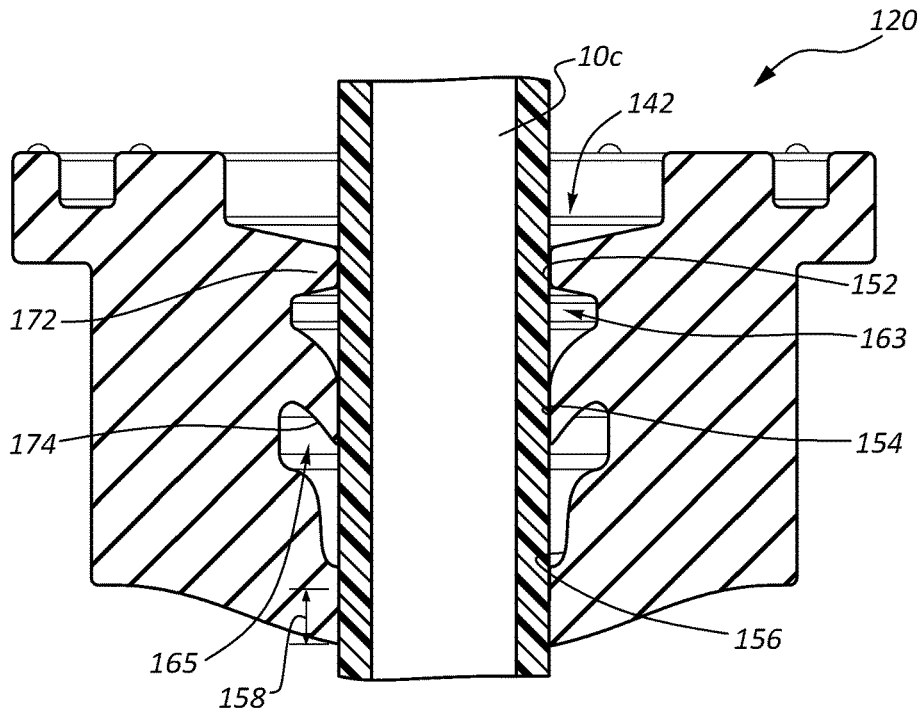
FIG. 5A is a cross-sectional front view of the elastomeric member of FIG. 2A with an elongate member of relatively large diameter extending therethrough.
Figure 5B:
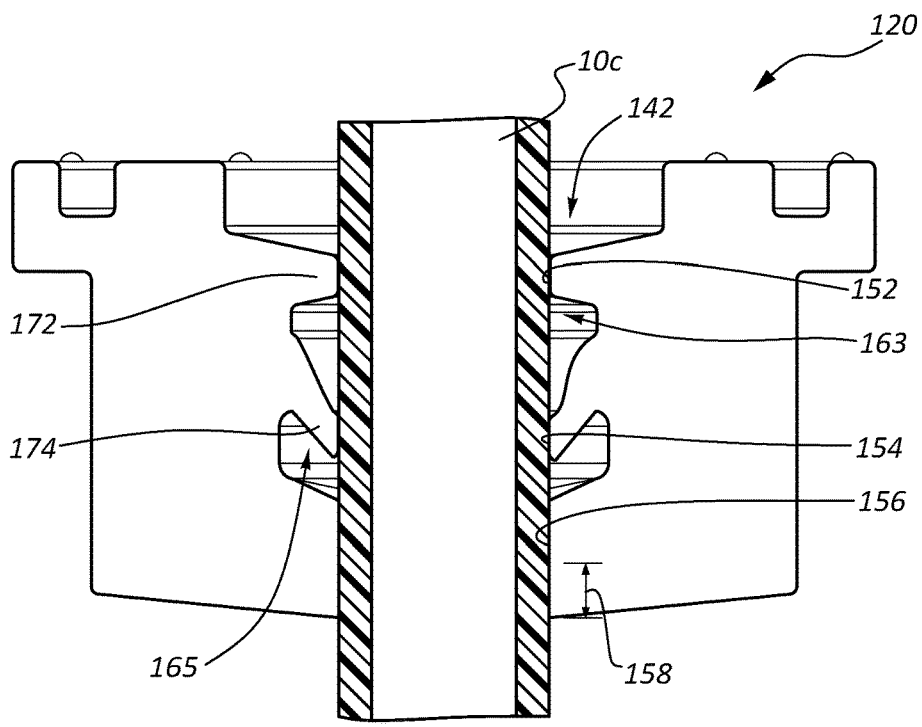
FIG. 5B is a cross-sectional side view of the elastomeric member of FIG. 5A with an elongate member of relatively large diameter extending therethrough.

FIGS. 5A and 5B provide alternative views of the elastomeric member 120 as an elongate member 10c of relatively large diameter extends across the elastomeric member 120. More particularly, FIG. 5A provides a cross-sectional front view of the elastomeric member 120 analogous to the view provided in FIG. 2C (i.e., perpendicular to the slit), while FIG. 5B provides a cross-sectional side view of the elastomeric member 120 analogous to the view provided in FIG. 2D (i.e., along the slit).

As can be seen in these figures, the first sealing surface 152 is sized to form a liquid-tight seal around the relatively large elongate member 10c. Due to the narrower diameter of the second sealing surface 154, the elongate member 10c distally displaces a portion the second protrusion 174 as the elongate member 10c is inserted into the channel 142 formed by the elastomeric member 120. For example, in the depicted embodiment, the second protrusion 174 bends into a second relief space 165 as the elongate member 10c is advanced within the elastomeric member 120.

Bending of the second protrusion 174 into the second relief space 165 may allow for strain relief as the elongate member 10c is advanced within the elastomeric member 120. For example, as the elongate member 10c is advanced within the elastomeric member 120, the second protrusion 174 may bend in a manner analogous to a hinge into the second relief space 165. The second relief space 165 may thus minimize or otherwise limit the amount of strain imposed on the elastomeric member 120 (or portions thereof) as the elongate member 10c is advanced within the elastomeric member 120. In this manner, a relief space (e.g., second relief space 165) for accommodating bending of a protrusion (e.g., second protrusion 174) may increase the tear-resistance of an elastomeric member 120.

The portions of elastomeric member 120 that contact one another to form the sealing zone 158 may also deflect distally into open space below the elastomeric member 120 as the elongate member 10c is inserted across the elastomeric member 120.

In the depicted embodiment, neither the second sealing surface 154 nor the third sealing surface 156 forms a liquid-tight seal around the elongate member 10c, as placement of the elongate member 10c across the elastomeric member 120 causes widening of the slit, thereby allowing blood to flow past the third sealing surface 156 and the second sealing surface 154. In other words, pathways analogous to the pathways 194 described above in connection with FIG. 4D may form as a result of an elongate member 10c that extends through the elastomeric member 120. However, the liquid-tight seal formed by the first sealing surface 152 prevents liquid from passing proximally past the first protrusion 172.

Thus, as shown in FIGS. 3A-5B, the elastomeric member 120 may be configured to form a liquid-tight seal around elongate members 10a, 10b, 10c of different diameter. The elastomeric member 120 may analogously be configured to form a liquid-tight seal around portions of a single elongate instrument wherein each portion of the elongate instrument has a different diameter.

The elastomeric member 120 is also configured to accommodate elongate members of diameter greater than the diameter of elongate member 10c. For example, as an elongate member of diameter greater than the diameter of elongate member 10c is advanced within a hemostasis valve assembly, the slit may widen, the first protrusion 172 may bend into a first relief space 163, the second protrusion 174 may bend into a second relief space 165, and portions of the elastomeric member that form the sealing zone 158 may bend into open space below the elastomeric member 120. In this fashion, elongate members having a diameter of greater than or equal to 9 Fr, 12 Fr, and/or 14 Fr may be inserted through the elastomeric member 120. For example, in some embodiments, an elongate member that includes a portion having a diameter of approximately 14 Fr may be inserted and retracted through the elastomeric member 120.

In some circumstances, an elongate member may be retracted from the elastomeric member 120. When the elongate member is retracted from the elastomeric member 120, one or more protrusions 172, 174 may bend toward the proximal end of the elastomeric member 120. In other words, the one or more protrusions 172, 174 may be configured to bend distally when the elongate member is advanced within the elastomeric member 120 and to bend proximally when the elongate member is retracted within the elastomeric member 120.

Figure 6A:
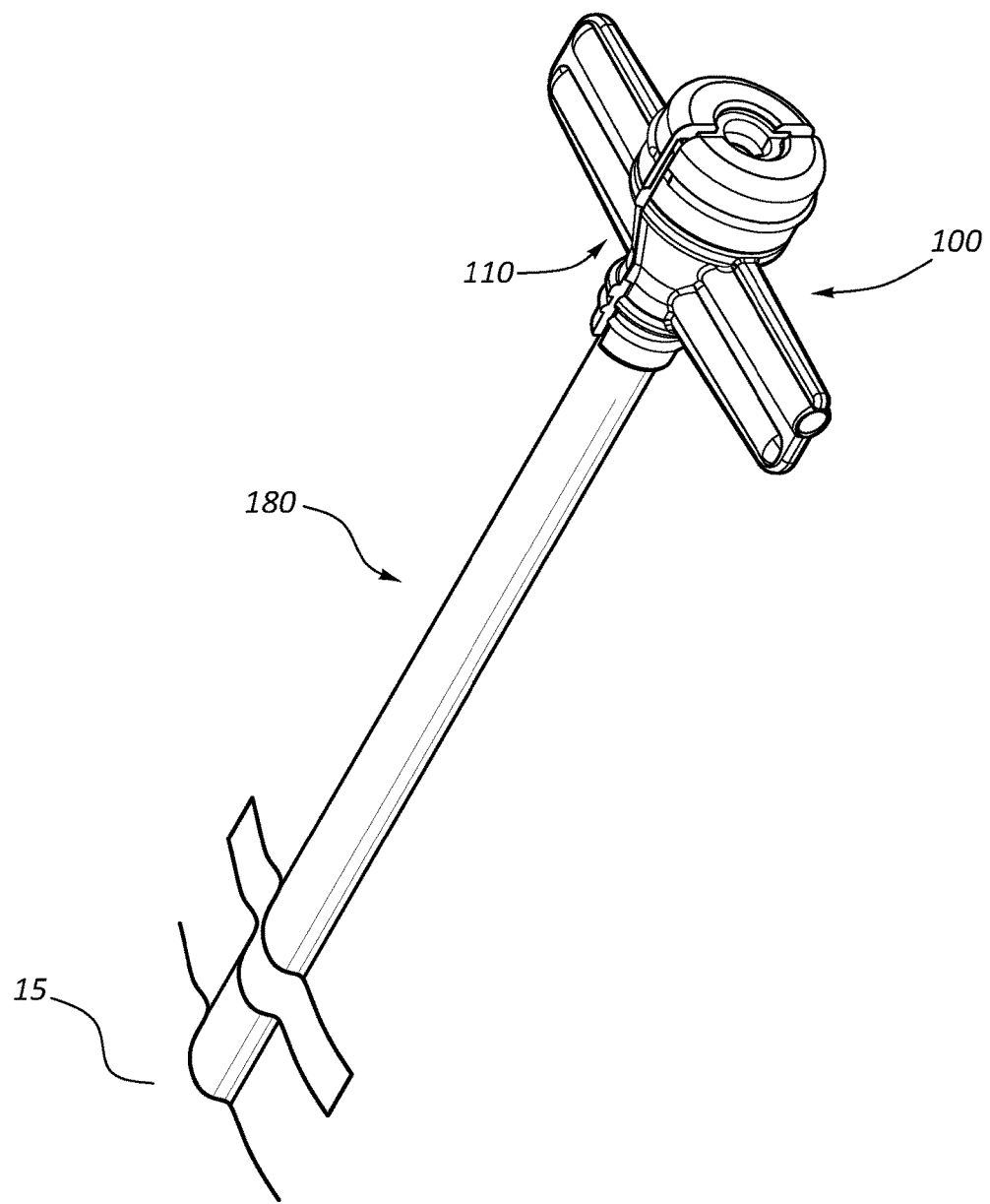
FIG. 6A is a perspective view of a hemostasis valve assembly coupled to an introducer sheath that has been inserted into a patient.
Figure 6B:
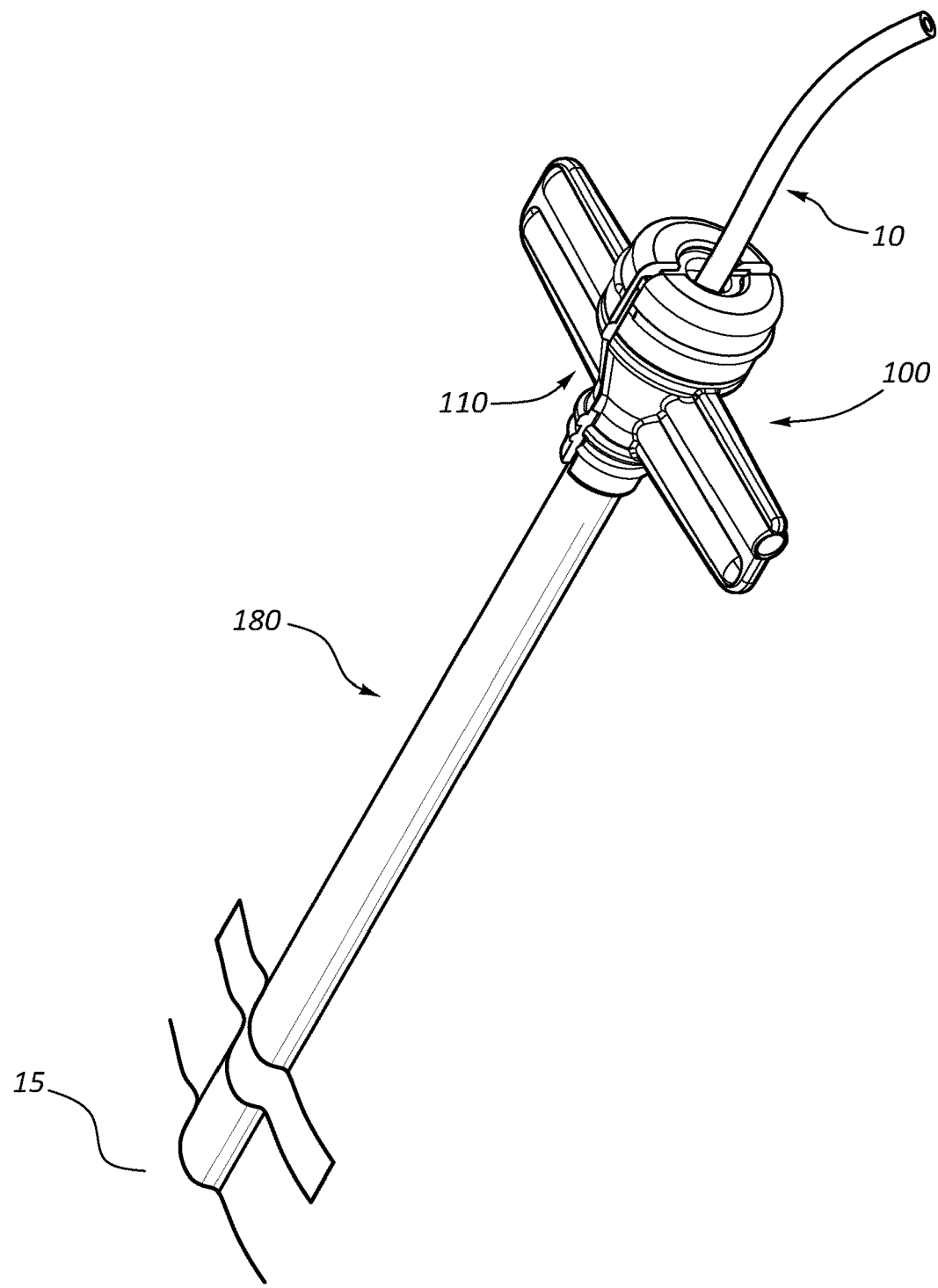
FIG. 6B is a perspective view of the hemostasis valve assembly and introducer sheath of FIG. 6A with an elongate member extending therethrough.
Figure 6C:
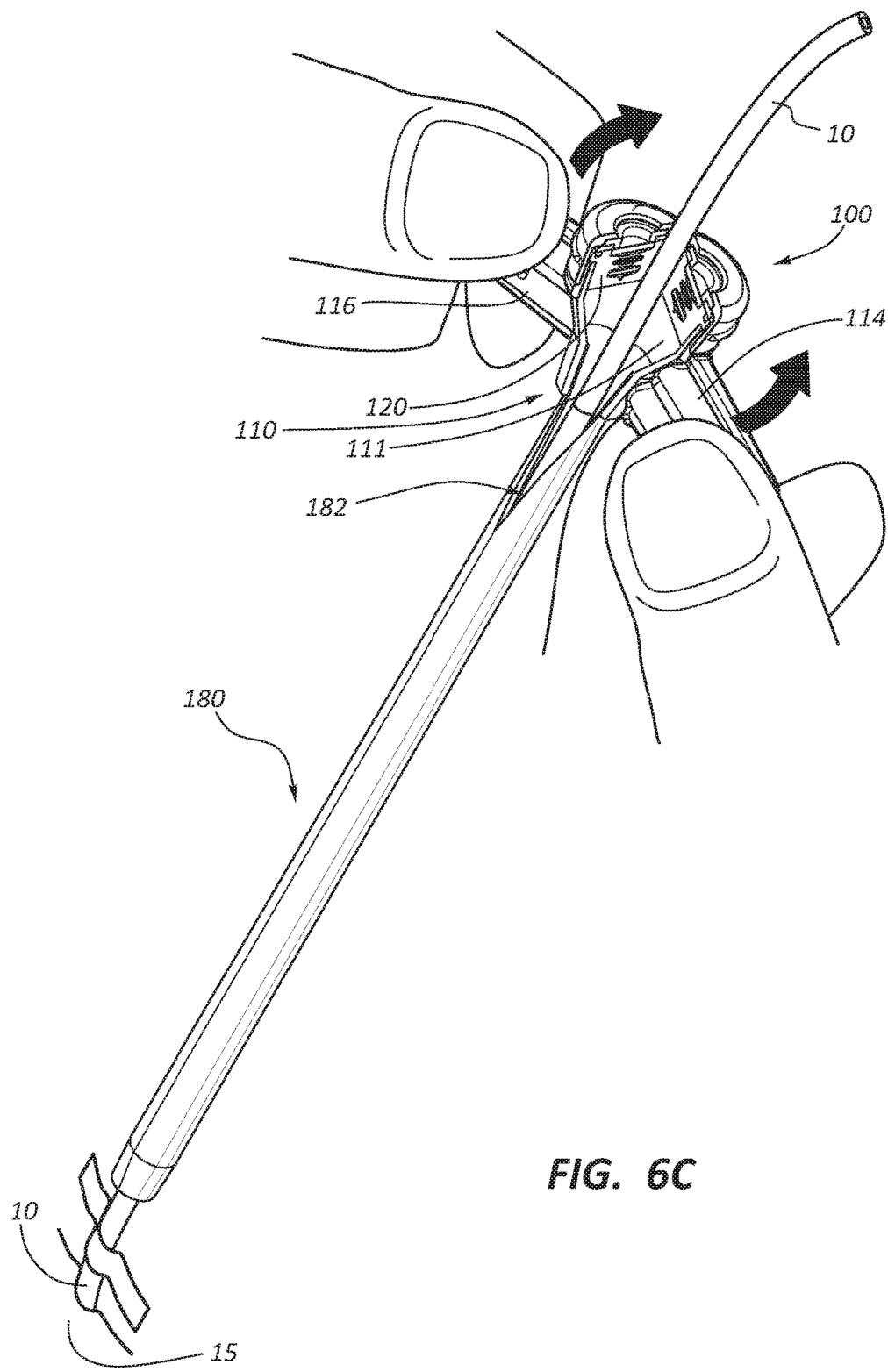
FIG. 6C is a perspective view of the hemostasis valve assembly, introducer sheath, and elongate member of FIG. 6B in which the hemostasis valve assembly is split to facilitate removal of the hemostasis valve assembly from around the elongate member.

FIGS. 6A-6C provide perspective views of a hemostasis valve assembly 100 and an introducer sheath 180 in various states. For example, FIG. 6A depicts a hemostasis valve assembly 100 that is coupled to an introducer sheath 180. More particularly the housing 110 (or hub) of the hemostasis valve assembly 100 may be coupled to a proximal end of the introducer sheath 180. In FIG. 6A, the introducer sheath 180 has been inserted into the vasculature of a patient 15, thereby providing an access site for inserting one or more medical instruments into the vasculature of the patient 15.

In FIG. 6B, an elongate member 10 has been inserted through the proximal end of the hemostasis valve assembly 100 and advanced within the introducer sheath 180 into the vasculature of the patient 15. In some embodiments, the elongate member 10 is an elongate medical instrument. For example, the elongate member 10 may be a guidewire, a catheter, a balloon catheter, a stent, a filter, or some other medical implement. When the elongate member 10 has been inserted into the vasculature of the patient, the practitioner may use the elongate member 10 to carry out any number of medical procedures. When a portion of the elongate member 10 is disposed across the hemostasis valve assembly 100, one or more of the first sealing surface, the second sealing surface, and the third sealing surface may form a liquid-tight seal around that portion of the elongate member 10.

In some circumstances, it may be advantageous to remove the introducer sheath 180 and hemostasis valve assembly 100 from around the elongate member 10. In some embodiments, it may be impractical or impossible to remove the hemostasis valve assembly 100 and/or introducer sheath 180 from around the elongate member 10 by retracting such components over a proximal end of the elongate member 10. For example, in some circumstances, the proximal end of the elongate member 10 may be coupled to a device or other component that is much larger than the hemostasis valve assembly 100.

As shown in FIG. 6C, the hemostasis valve assembly 100 may, in such circumstances, be removed from around the elongate member 10 by splitting, tearing, breaking, or otherwise separating portions of the hemostasis valve assembly 100 from one another. For example, in the depicted embodiment, a practitioner may apply a first force to a central region 111 of the housing 110 and opposing forces on the arms 114, 116 of the housing 110, thereby causing the housing 110 to break and/or snap. The practitioner may also split the introducer sheath 180. For example, the practitioner may withdraw the introducer sheath 180 from the patient and make a longitudinal cut 182 along the length of the introducer sheath 180. In some instances, the introducer sheath 180 includes a scored line or a weakened region to facilitate making of the longitudinal cut 182. In some instances, the scored line or weakened region is aligned with the reduced-thickness portions 118, 119 of the housing to facilitate separation. Once (1) portions of the housing 110 have been separated from one another (e.g., via breakage) and (2) the introducer sheath has been cut along its length, the housing 110 of the hemostasis valve assembly 100 and the introducer sheath 180 may be removed from the elongate member 10 without retracting such components over a proximal end of the elongate member 10. The elastomeric member 120 may likewise be removed from around the elongate member 10.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to an "embodiment" means that a particular feature, structure, or characteristic described in connection with that embodiment is included in at least one embodiment. Thus, the quoted phrase, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A hemostasis valve assembly comprising:
   a housing;
   an elastomeric member at least partially disposed within the housing, the elastomeric member forming a variable-width channel that extends at least partway through the elastomeric member;
   wherein the elastomeric member comprises:
      a first sealing surface defining a first diameter;
      a first relief surface defining a second diameter that is larger than the first diameter;
      a second sealing surface defining a third diameter, wherein the third diameter differs in size from the first diameter and is smaller than the second diameter; and
      a second relief surface defining a fourth diameter that is larger than the third diameter;
   wherein the first sealing surface is proximal of the first relief surface, the first relief surface is proximal of the second sealing surface, and the second sealing surface is proximal of the second relief surface; and
   a foam member configured to secure the elastomeric member at least partially within the housing,
   wherein the foam member provides structural support against the proximal end of the elastomeric member.

2. The hemostasis valve assembly of claim 1, wherein the elastomeric member is radially compressed inward by the housing.

3. The hemostasis valve assembly of claim 1, further comprising a slit in the elastomeric member that extends at least from a distal end of the elastomeric member to a distal end of the channel.

4. The hemostasis valve assembly of claim 3, wherein the slit divides the elastomeric member into two separate unconnected pieces.

5. The hemostasis valve assembly of claim 4, wherein the elastomeric member further comprises a sealing zone, wherein the sealing zone forms a liquid-tight seal across the slit when the hemostasis valve assembly is in a resting state.

6. The hemostasis valve assembly of claim 1, further comprising a cap that is configured to secure the elastomeric member at least partially within the housing and a splittable introducer sheath coupled to the housing.

7. The hemostasis valve assembly of claim 1, wherein the elastomeric member is configured to be removed from around an elongate member that extends through the elastomeric member without being retracted over a proximal end of the elongate member.

8. The hemostasis valve assembly of claim 7, wherein the housing comprises a first arm and a second arm, wherein the first arm and the second arm are configured to separate portions of the housing from one another to permit removal of the housing from the elongate member without retracting the housing over the proximal end of the elongate member.

9. The hemostasis valve assembly of claim 1, wherein the housing radially compresses the elastomeric member toward a longitudinal axis of the valve assembly such that the width of the elastomeric member is between 97% and 94% of the width of the elastomeric member when uncompressed.

10. The hemostasis valve assembly of claim 1, wherein the first sealing surface is defined by an innermost surface of a first protrusion and the second sealing surface is defined by an innermost surface of a second protrusion, wherein the first protrusion is configured to bend into a first relief space formed by the first relief surface, and wherein the second protrusion is configured to bend into a second relief space defined by the second relief surface as an elongate member is advanced within the hemostasis valve assembly.

11. The hemostasis valve assembly of claim 1, wherein the first diameter is larger than the third diameter.

12. The hemostasis valve assembly of claim 1, wherein the elastomeric member further comprises a third sealing surface having a fifth diameter that differs from the diameter of the first sealing surface and the second sealing surface, wherein the third sealing surface is distal of the second relief surface.

13. The hemostasis valve assembly of claim 12, wherein the fifth diameter is smaller than both the first diameter and the third diameter.

14. The hemostasis valve assembly of claim 13, wherein the fifth diameter is configured to form a liquid-tight seal around a guidewire.

15. The hemostasis valve assembly of claim 1, wherein the first sealing surface forms a first cylindrical surface having a first height of between 0.25 mm and 1.5 mm, and the second sealing surface forms a second cylindrical surface having a second height of between 0.25 mm and 1.5 mm.

16. The hemostasis valve assembly of claim 1, wherein the foam member is donut shaped.

17. A hemostasis valve assembly comprising:
   an elastomeric member, wherein the elastomeric member comprises:
      a first sealing surface defined by an innermost surface of a first inward-extending protrusion;
      a first relief surface distal of the first sealing surface;
      a second sealing surface defined by an innermost surface of a second inward-extending protrusion; and
      a second relief surface distal of the second sealing surface;
   wherein the first protrusion is configured to bend into a first relief space formed by the first relief surface, and wherein the second protrusion is configured to bend into a second relief space defined by the second relief surface as an elongate member is advanced within the hemostasis valve assembly; and
   a housing comprising a foam member configured to secure the elastomeric member at least partially within the housing,
   wherein the foam member is disposed proximal to the elastomeric member.

18. The hemostasis valve assembly of claim 17, wherein the elastomeric member is at least partially disposed within an inner surface of the housing and wherein the elastomeric member is radially compressed by the inner surface.

19. The hemostasis valve assembly of claim 17, further comprising a slit that divides the elastomeric member into two separate unconnected pieces.

\* \* \* \* \*